United States Patent
Baldus et al.

(10) Patent No.: US 8,308,640 B2
(45) Date of Patent: Nov. 13, 2012

(54) SYSTEM FOR AUTOMATIC CONTINUOUS AND RELIABLE PATIENT IDENTIFICATION FOR ASSOCIATION OF WIRELESS MEDICAL DEVICES TO PATIENTS

(75) Inventors: Heribert Baldus, Aachen (DE); Karin Klabunde, Aachen (DE); Olaf Such, Aachen (DE); Guido Musch, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1628 days.

(21) Appl. No.: 11/575,658

(22) PCT Filed: Sep. 19, 2005

(86) PCT No.: PCT/IB2005/053075
§ 371 (c)(1), (2), (4) Date: Mar. 21, 2007

(87) PCT Pub. No.: WO2006/035351
PCT Pub. Date: Apr. 6, 2006

(65) Prior Publication Data
US 2009/0184842 A1    Jul. 23, 2009

Related U.S. Application Data

(60) Provisional application No. 60/614,629, filed on Sep. 30, 2004.

(51) Int. Cl.
*A61B 5/00* (2006.01)
(52) U.S. Cl. .......... 600/300; 600/301; 340/539.12; 705/2

(58) Field of Classification Search .......... 600/300–301; 340/539.12–539.14; 705/2–5
See application file for complete search history.

(56) References Cited

U.S. PATENT DOCUMENTS

| | | | |
|---|---|---|---|
| 5,423,334 A | 6/1995 | Jordan | |
| 5,796,827 A * | 8/1998 | Coppersmith et al. | 713/182 |
| 5,833,603 A | 11/1998 | Kovacs et al. | |
| 7,051,120 B2 * | 5/2006 | Greene et al. | 709/250 |
| 7,163,511 B2 * | 1/2007 | Conn et al. | 600/309 |
| 7,425,200 B2 * | 9/2008 | Brockway et al. | 600/486 |
| 7,480,492 B2 * | 1/2009 | Williams et al. | 455/100 |
| 7,684,754 B2 * | 3/2010 | Glass et al. | 455/41.2 |

(Continued)

FOREIGN PATENT DOCUMENTS

DE    19523965 A1    8/1996

(Continued)

OTHER PUBLICATIONS

Baskiyar, S.; A Real-Time Fault Tolerant Intra-Body Network; 2002; IEEE Conf. on Local Computer Networks; pp. 235-240.

*Primary Examiner* — Henry M Johnson, III
*Assistant Examiner* — Bobby Soriano

(57) ABSTRACT

The medical communication system comprises a plurality of medical identification devices (12). Each identification device (12) is attached to one particular patient (14). A registration processor generates a unique patient identification data that is stored in an electronic patient identification code memory (54). Each identification device (12) includes an intra-body wireless communication device (16) which transmits the patient's identification on the patient's body. A medical device (22), which is linked to the patient (14) to measure a vital function, periodically automatically receives the patient's identification code to continually ensure association to a correct patient.

19 Claims, 4 Drawing Sheets

U.S. PATENT DOCUMENTS

| | | | |
|---|---|---|---|
| 7,779,450 B2 * | 8/2010 | Ohmori | 726/2 |
| 7,822,983 B2 * | 10/2010 | Aull et al. | 713/172 |
| 7,889,069 B2 * | 2/2011 | Fifolt et al. | 340/539.12 |
| 2002/0084904 A1 | 7/2002 | De La Huerga | |
| 2003/0125017 A1 | 7/2003 | Greene et al. | |
| 2004/0176667 A1 * | 9/2004 | Mihai et al. | 600/300 |
| 2004/0193453 A1 | 9/2004 | Butterfield et al. | |
| 2005/0101844 A1 * | 5/2005 | Duckert et al. | 600/300 |
| 2005/0137464 A1 * | 6/2005 | Bomba | 600/300 |
| 2005/0159789 A1 * | 7/2005 | Brockway et al. | 607/32 |
| 2005/0192649 A1 * | 9/2005 | Shehadeh et al. | 607/60 |
| 2005/0278194 A1 * | 12/2005 | Holland et al. | 705/2 |
| 2006/0031378 A1 * | 2/2006 | Vallapureddy et al. | 709/208 |
| 2007/0013519 A1 * | 1/2007 | Chung et al. | 340/572.1 |
| 2007/0184831 A1 * | 8/2007 | Morimoto | 455/432.1 |

FOREIGN PATENT DOCUMENTS

| | | |
|---|---|---|
| DE | 19932147 A1 | 1/2001 |
| WO | 0058901 A1 | 10/2000 |

\* cited by examiner

SYSTEM FOR AUTOMATIC CONTINUOUS AND RELIABLE PATIENT IDENTIFICATION FOR ASSOCIATION OF WIRELESS MEDICAL DEVICES TO PATIENTS

CROSS REFERENCE TO RELATED APPLICATIONS

This application claims the benefit of U.S. provisional application Ser. No. 60/614,629 filed Sep. 30, 2004, which is incorporated herein by reference.

DESCRIPTION

The present invention relates to the medical monitoring systems and methods. It finds particular application in conjunction with the patient's identification and association to medical devices in health care facilities and will be described with particular reference thereto. However, it is to be appreciated that the invention will also find application in conjunction with patient monitoring in retirement communities, assisted living, at home, and the like.

Worldwide, the health care facilities employ new flexible care giving scenarios which allow the clinicians in the emergency units, for example, to quickly use a monitoring or diagnostic system. Traditionally, vital sign sensors were connected by wires with associated monitors and equipment. Telemetry patients, as another example, can locally be monitored by temporarily assigning a portable monitor or a PDA. Due to the inconvenience of the myriad of wires, there is an increasing demand for wireless telemetry. The care everywhere paradigm employs various wireless medical devices and sensors around the patient at the point-of-care.

Typically, a wireless sensor is attached to a patient to measure certain vital functions of the patient. The wireless medical sensors and devices use radio links for communication and transmission of data to other devices within the hospital system. Wireless devices allow an increased mobility of patients and clinicians through a more flexible usage of medical devices at different places, for different patients, or by different clinicians. In emergency treatment facilities, wireless communications can save time connecting and disconnecting sensors as a patient moves from ambulance, to trauma assessment station, to surgery, to recovery, to a hospital room, etc.

In the health care facilities, where the hardwired devices are used, it is easy to monitor which patient is associated to which medical device. In the wireless system, it is more difficult to verify which identification signal is coming from which patient. Several techniques have been proposed to associate a wireless device to the patient. One such technique is a single assignment through manual input of the patient information via keyboard or during a device start up process. Another such technique is a single assignment through a barcode marker which contains a unique identification number (ID) and is attached to the patient's body, e.g. with a wrist band. When a new device is used for a specific patient, the patient's ID is read with a special barcode reader and assigned to the new device. Yet another such solution is a single assignment through RFID—corresponds to barcode solution; the information (ID) is stored in an RFID-tag. These solutions have the problem of reliance on a manual process which is subject to a human error. In addition, the automatic association of the device to the patient is not feasible. It is also not possible to regularly check the association.

Automatic association of a wireless identification system is possible using Bluetooth or other short-range RF technology. The Bluetooth technology is well known in the art. E.g., a short-range RF-sender is attached to the patient's body to continuously send out the patient identification. Wireless medical devices in the environment of the patient can automatically receive the identification information and check/verify it regularly. However, because of the large spreading of the RF signal, sensors associated with the nearby patients can also receive the identification and associate with the wrong patient. Unambiguous association to a specific patient cannot be guaranteed.

The frequent and mobile usage of wireless/mobile medical equipment at the patient's bedside requires an efficient and safe procedure for association of the medical equipment to the respective patient. The present invention provides a new and improved apparatus and method which overcomes the above-referenced problems and others.

In accordance with one aspect of the present invention, a medical communications system is disclosed. The medical communication system comprises a plurality of medical identification devices. Each device is connected with one patient and includes an electronic patient identification code memory and a short-range, wireless communication device for communicating the patient identification. The medical communication system further comprises at least one medical device which is linked to a patient. A means automatically associates the medical device with the electronic patient identification code of the medical identification device connected to the same patient. A means automatically verifies the association of the medical device to the patient.

In accordance with another aspect of the present invention, a communication method is disclosed. A wireless patient identification device is assigned to a selected patient. The identification device is encoded with an electronic patient identification code that uniquely identifies the selected patient which it is assigned to. The wireless patient identification device is automatically associated to at least one medical device which is linked to the selected patient to measure at least a vital function. The association of the medical device to the selected patient is automatically verified.

One advantage of the present invention resides in automatic association of medical devices to patients with no need for a manual input of patient identification.

Another advantage resides in periodic automatic verification of the association of the medical device to the patient.

Another advantage resides in continuous secure and reliable patient identification on or close to the patient's body.

Another advantage resides in speeding up the use of medical devices.

Another advantage resides in non-contact transmission of the patient information.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
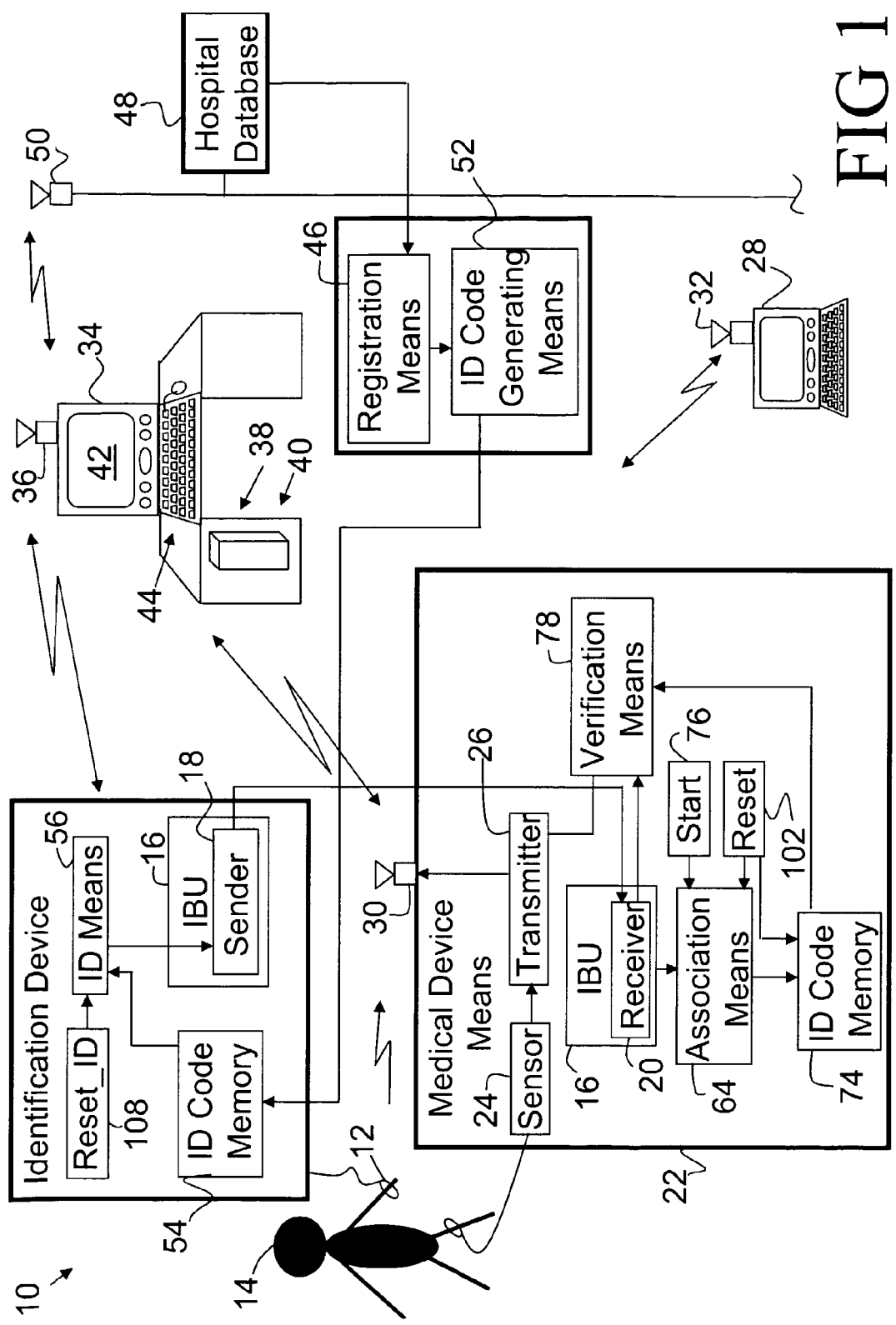
FIG. 1 is a diagrammatic illustration of an identification system.

With reference to FIG. 1, a patient identification system 10 includes a plurality of identification devices or IDDs 12. Each identification device 12 is attached to a patient or patient's body 14 as a band at a wrist, leg, or the like. Alternatively, the identification device 12 is a non-contact device and is attached in a close proximity, e.g. within 10 cm, of the patient's body 14. Each identification device 12 includes a sender 18 of an intra-body communication unit or IBU 16. The intra-body communication unit 16 utilizes a near-field body-communication technology, which is based on capacitive coupling and well known in the art, to transmit the patient's ID. In regular time intervals T, e.g. every 1 sec, the sender 18 sends a unique identification signal. The ID signal is received by a receiver 20 of another intra-body communication unit 16, which is connected to a medical device or PWD or medical device means 22. The medical device means 22 such as ECG, blood oxygen sensor, pulse monitor, injection pump, a drip monitor, or the like, has a sensor 24 which is typically disposed in close proximity to or contacting the patient 14 for continuous vital sign measurements. The medical device 22 includes a transmitter 26, which wirelessly transmits the vital sign measurements to a bedside-monitor 28 via a transmitting/receiving link 30, 32 or to a central station 34 via transmitting/receiving link 30, 36. The central station 34 is equipped with an appropriate hardware 38, software 40, monitor 42 and input means 44. In one embodiment, the medical device means 22 is a mobile device that can be directly attached to the patient 14, such as a wireless vital sign sensor, or positioned permanently or temporarily in close proximity of the patient 14, such as a spot-measurement unit, and can be equipped with the intra-body unit receiver 20.

Typically, when the patient 14 is admitted to the health care facility, a registration means 46 configures a corresponding identification device 12. More specifically, the registration means 46 is connected with a Departmental, Clinical or Hospital Information system which includes a hospital database 48, preferably wirelessly via communications link 36, 50. An ID code generating means 52 generates a unique patient's identification number which is associated to a corresponding patient record in the information system 48. Optionally, the ID code generating means 52 generates a comprehensive patient identification code by a use of a set of patient data, e.g. patient's name, date of birth, and/or other hospital data or medical patient data. The generated unique identification number or comprehensive patient identification code is stored in an ID code memory 54 of the patient's associated identification device 12. An ID means or identification process 56 performs an initial identification of the identification device 12. After the identification process 56 is completed, the identification device 12 is attached to the patient's body 14. As each medical device 22 is attached to the patient 14, the identification device 12 sends the patient ID to the medical device 22 to associate it with the same patient ID. Periodically, the patient's ID is verified.

Figure 3:
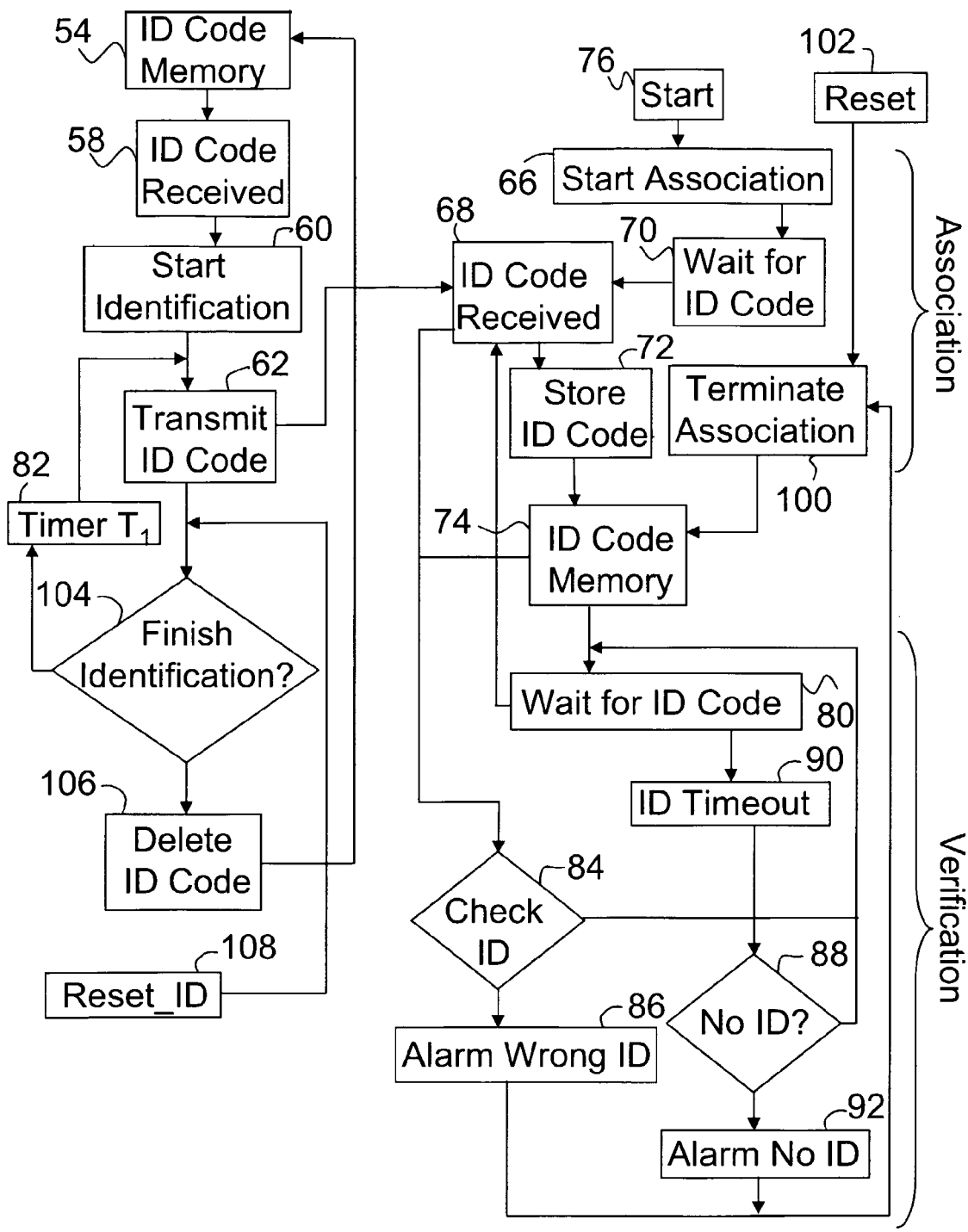
FIG. 3 is a diagrammatic illustration of a second identification system.

With continuing reference to FIG. 1 and further reference to FIG. 3, the ID code is received 58 by the identification means 56 from the ID code memory 54. The identification process 56 is started 60. The ID code is transmitted 62 to the medical device 22 by the intra-body unit sender 18. An association means or process 64 automatically starts 66 the association of the medical device 22 to the patient 14 when the ID code is received 68 by the intra-body unit receiver 20. More specifically, the association means 64 waits 70 for receiving the ID code. The intra-body unit receiver 20 disposed at the medical device 22 receives 68 the patient's ID code. The ID code is stored 72 in an ID code memory 74 of the medical device 22. Optionally, the ID code is transmitted via the communication link 30, 32; 30, 36 to the bedside monitor 28 and/or to the central station 34 to automatically display the patient ID number, patient name, etc., so that the device association process can be recorded or verified by a human. In one embodiment, the association process 64 is optionally manually initiated with a use of a start button 76.

Once the medical device 22 is associated with the patient's ID, it starts communicating the sensed information by communication link 30, 32; 30, 36 to the bedside monitor 28 and/or the central station 34. Alternatively, all of the information sensed by all of the medical devices 22 associated with the same patient 14 can be communicated with the near body technology to a common medical device or the ID device which, in turn, transmits all of the monitored information to the bedside monitor 28 and/or central station 34. Communications with the bedside monitor 28 and the central station 34 include the patient ID code to keep the information segregated by the patient.

A verification means or process 78 verifies the association of the medical device 22 to the patient 14 on a regular basis during the normal operation of the medical device 22. More specifically, the verification means 78 waits 80 for the ID code. In one embodiment, so long as the medical device 22 is at the patient 14 or close to the patient 14, the medical device 22 receives 68 the ID code in regular $T_1$ time intervals 82. Alternatively, the medical device 22 can periodically query the identification device 12 to request the transmission of the patient's ID. The ID code is checked 84. If the received ID code is different from the stored ID code, an alarm "wrong ID" is raised 86 locally at the medical device 22 as well as at the bedside monitor 28 and/or central station 34. If no ID code is being received 88, the medical device 22 waits for reception for the pre-specified period of time $T_2$, e.g. ID timeout 90 such as 15 sec. If no ID code is received during the $T_2$ period, an alarm "no ID" is raised 92. After any alarm 86, 92, an explicit re-execution of the association process 64, which preferably is manually triggered by the start button 76, is performed. If after the alarm is raised 86, 92, the ID code is being received again, it is slayed until the association process 64 is re-executed. The association of the medical device 22 to the patient 14 is preferably terminated 100 manually by a reset button 102. As a result, the ID code is erased from the ID code memory 74. It is also contemplated that the association of the medical device 22 to the patient 14 can be manually terminated through a control device such as a dedicated user interface at the bedside monitor 28, central station 34, clinician's PDA, or other like device. Each termination or disassociation is reported to the central station 34. When the patient leaves the facility or the identification code is to be terminated 104, the ID device 12 can be destroyed or it can be reset by deleting 106 the ID code in the identification device memory 54. It is performed manually by a use of a reset_ID button 108. Optionally, the identification process 56 is terminated by deleting the stored information via a dedicated procedure at the central station 34, or other appropriate procedure. If the device is reusable, it is preferably reprogrammed by the registration means 46 as it is given to another patient.

Figure 2:
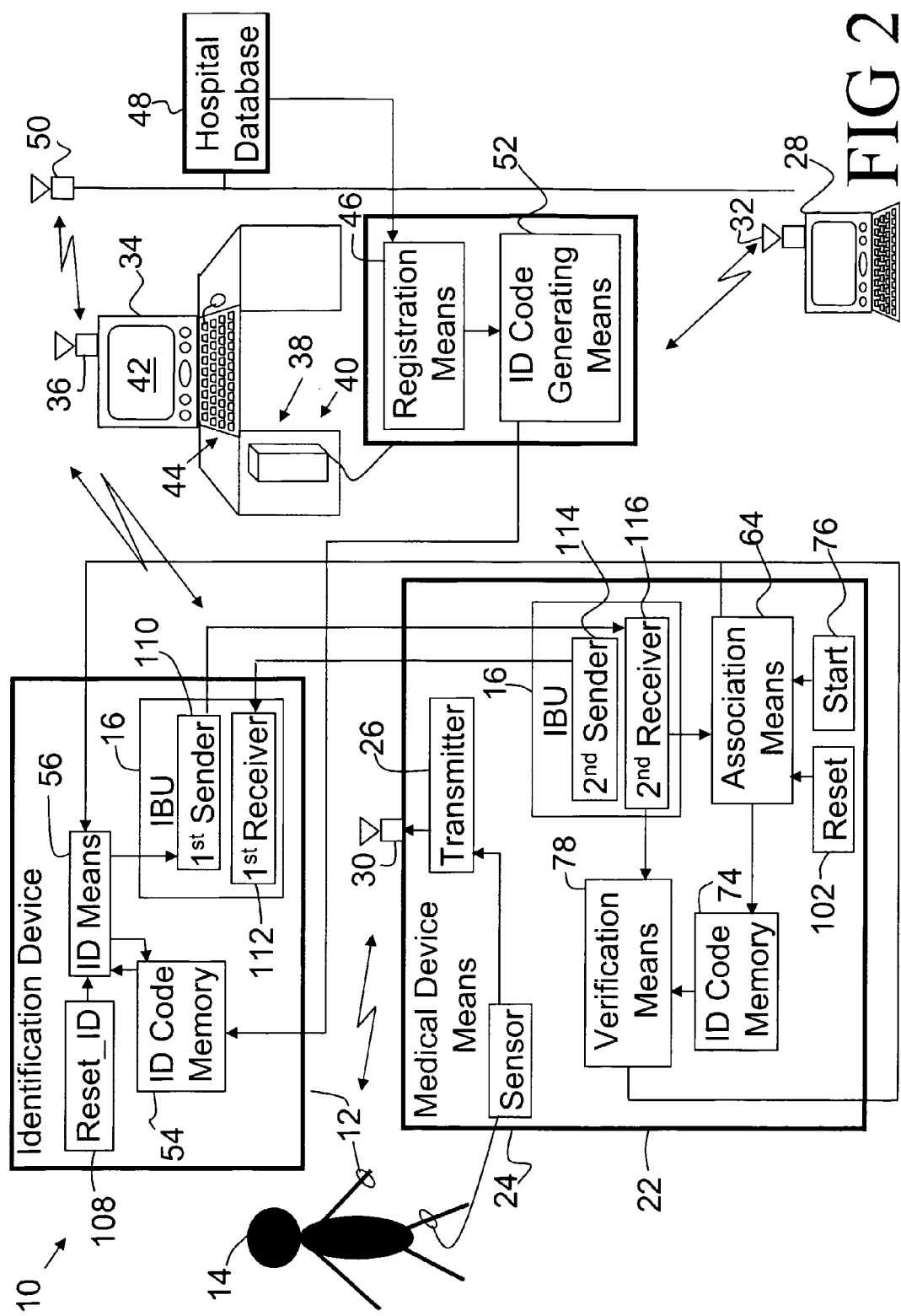
FIG. 2 shows a process flow of the identification system.
Figure 4:
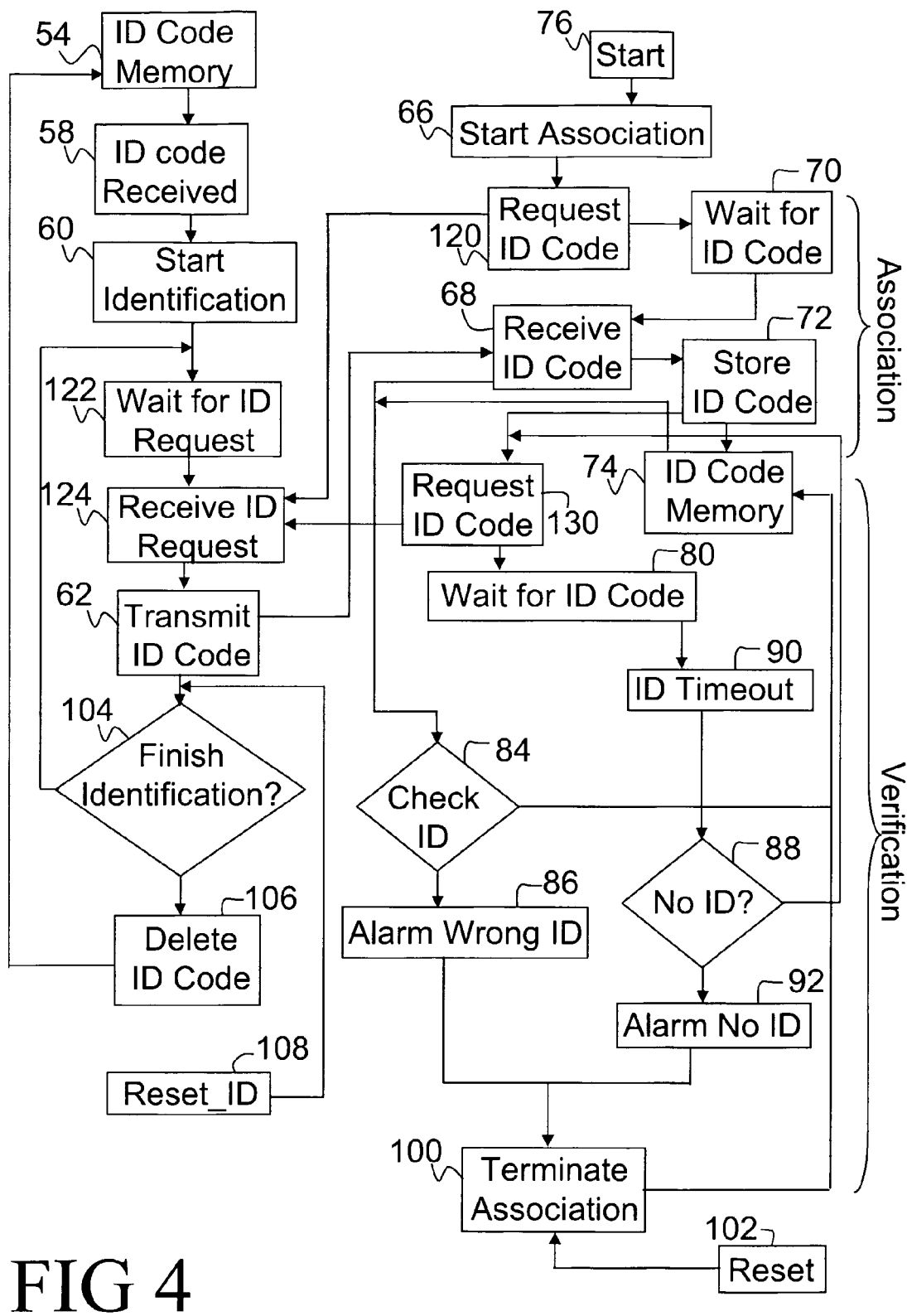
FIG. 4 shows a process flow of the second identification system.

With reference to FIGS. 2 and 4, each patient 14 is equipped with the identification device 12, which is attached to the patient's body 14 or close to the patient's body. The identification device 12 includes a first intra-body unit sender/receiver 110, 112. Each medical device 22, which is attached to the patient 14, includes a second intra-body unit sender/receiver 114, 116. The ID code is transmitted 62 via the first intra-body unit sender 110 upon request 120 of the medical device 22.

More specifically, the identification device 12 waits 122 for an ID code request to be received 124 by the first intra-body unit receiver 112. The medical device 12 submits the ID code request via the second intra-body unit sender 114. When the first intra-body unit receiver 112 receives the request 124, the first intra-body unit sender 110 sends 62 the ID code to the medical device 22. The second intra-body unit receiver 116 receives 68 the ID code, after which the ID code is stored 72 in the medical device ID code memory 74. The verification process 78 verifies the continued association of the medical device 22 to the patient 14 on a regular basis during the normal operation of the medical device 22. More specifically, in regular time intervals $T_3$, the second intra-body unit sender 114 submits 130 the ID code request to the identification device 12. Upon receiving 124 of the request by the first intra-body unit receiver 112, the first intra-body unit sender 110 sends 62 the ID code to the medical device 22. The ID code is received 68 by the second intra-body unit receiver 116. The received ID code is checked 84. If the received ID code is different from the stored ID code, an alarm "wrong ID" is raised 86 locally at the medical device 22 as well as at the bedside monitor 28 and/or central station 34. If no ID code is being received 88 during the preset time $T_2$, the medical device 22 repeats the ID code request 130 for a pre-defined number of times N.

For security and privacy, the communications between the identification device 12 and the medical device 22 are preferably encrypted. Preferably, a group of identification devices 12 and medical devices 22 is pre-configured with a shared security key which might be specific for each medical department, or for the overall hospital. The shared key is used for encrypting/decrypting the ID code. This ensures that only authorized devices can send/receive the valid ID code.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

Having thus described the preferred embodiments, the invention is now claimed to be:

1. A medical communications system comprising:
   a plurality of patient identification devices, each connected with and carried by one patient and including:
      a patient identification device electronic patient identification code memory which stores a patient identification code for the one patient; and
      an intra-body communication device including:
         an intra-body communications transmitter capacitively coupled to a body of the one patient to transmit data over the one patient's body using near-field body communications; and
         a patient identification device processor which controls the intra-body communications transmitter to retrieve the patient identification code from the patient identification device electronic patient identification code memory and transmit the patient identification code on the one patient's body; and
   at least one medical device which is connected with and carried by the one patient, each medical device including:
      a medical device electronic patient identification code memory;
      a medical device intra-body communication receiver which receives the patient identification code transmitted using the near-field communications on the one patient's body; and
      a medical device processor which (1) initially causes the medical device electronic patient identification memory to store the patient identification code received by the medical device intra-body communications receiver and (2) subsequently automatically verifies that the patient identification code stored in the medical device patient identification code memory matches each patient identification code subsequently received from the patient identification device intra-body communications transmitter to verify that the patient identification code stored in the medical device patient identification code memory identifies the one patient.

2. The system as set forth in claim 1, wherein the device further includes:
   a wireless short-range communication device for communicating patient and device status to a central patient monitor displayed from the one patient.

3. The system as set forth in claim 1, wherein the patient identification device processor periodically triggers the patient identification device transmitter to retransmit the patient identification code stored in the patient identification device patient identification code memory.

4. The system as set forth in claim 1, wherein the medical device furthers includes a medical device intra-body communications transmitter and the patient identification device includes a patient identification device receiver and wherein the medical device processor periodically controls the medical device transmitter to:
   transmit a request to the patient identification device receiver to request the patient identification device processor to cause the patient identification device transmitter to transmit the patient identification code stored in the patient identification device patient identification code memory.

5. The system as set forth in claim 1, wherein the medical device processor further terminates a linkage of the medical device to the patient identification device in response to one of:
   the received patient identification code being different from the patient identification code stored in the medical device patient identification memory,
   the patient identification code not being received within a pre-specified time period, and
   a manual reset being received.

6. The system as set forth in claim 1, further including:
   an initialization device which generates the electronic patient identification code based on at least a record data of the one patient in an information database and which loads the electronic patient identification code into the electronic patient identification code memory of the patient identification device prior to the patient identification device being connected with the one patient.

7. The system as set forth in claim 1, wherein the medical device further includes:
   a sensor which senses one of measuring a vital function of the one patient;
   a transmitter which wirelessly transmits a signal carrying the measured vital function and the patient identification code from the medical device patient identification code memory to a bed-side device.

8. A communication method comprising:
assigning a wireless patient identification device to a selected patient wherein the identification device is encoded with an electronic patient identification code that uniquely identifies the selected patient to which the identification device is assigned;
attaching the wireless patient identification device to one part of the selected patient;
attaching at least one wireless medical device to at least one other part of the selected patient;
wherein the patient identification devices and the medical device are capacitively coupled with the selected patient and communicate over the patient using near-field intra-body communications;
automatically associating the wireless patient identification device to the at least one medical device by storing the electronic patient identification code of the selected patient in a memory of the medical device; and
automatically verifying the association of the medical device to the selected patient including:
subsequently transmitting the electronic patient identification code from the patient identification device to the medical device using the near-field intra-body communications,
receiving the subsequently transmitted electronic patient identification code at the medical device, and
with a processor of the medical device, comparing the subsequently received electronic patient identification code with the stored electronic patient identification code in the medical device memory.

9. The method as set forth in claim 8, wherein the associating step includes:
periodically transmitting via the near-field intra-body communications the patient identification code from the patient identification device.

10. The method as set forth in claim 9, further including:
receiving a first transmitted patient identification code by the at least one medical device; and
storing the first received patient identification code in an electronic patient ID code memory of the medical device.

11. The method as set forth in claim 10, wherein the verifying step includes:
periodically receiving the patient identification code subsequently transmitted by the patient identification device; and
comparing the stored patient identification code and the subsequently received patient identification codes.

12. The method as set forth in claim 11, further including:
terminating the association of the medical device to the patient when one of:
the received patient identification code is different from the stored patient identification code,
the identification code is not received within a pre-specified time period, and
manually actuated through a control device by the clinician.

13. The method as set forth in claim 12, wherein the termination step includes:
erasing the patient identification code from the medical device identification code memory; and
reporting the termination to at least one of a bedside monitor and a central station.

14. A medical communications system comprising:
patient identification devices;
medical devices; and
one or more processors programmed to perform the method of claim 8.

15. The method as set forth in claim 8, wherein the assigning step includes:
generating a unique electronic identification code for the patient based on at least a data record of the patient in an information database; and
storing the patient identification code in a patient identification device electronic patient identification code memory.

16. A medical communications system comprising:
at least one medical device configured to be attached to a patient, the medical device including:
a sensor which measures a vital sign of the patient;
a medical device patient code memory which stores a patient identification code of the patient;
a medical device receiver which receives communications carrying the patient identifier code; and
a medical device transmitter which wirelessly transmits a signal carrying the vital signs from the sensor and the patient identification code from the medical device patient code memory to an off-patient monitor device;
a patient identification device configured to be attached to the patient, the patient identification device including:
a patient identification device electronic patient identification code memory which stores the patient identification code for the patient; and
a transmitter which wirelessly transmits the patient identification code from the patient identification device electronic identification code memory; and
a patient identification device processor which controls the transmitter to retrieve the patient identification code from the patient identification device electronic patient identification code memory and transmit the patient identification code to the at least one medical device; and
wherein the medical device further includes:
a medical device processor which is connected to the medical device receiver to receive the patient identification code subsequently transmitted by the patient identification device transmitter and verify that the patient identification code stored in the medical device patient code memory matches the received patient identification code.

17. The system as set forth in claim 16, further including:
a plurality of the medical devices, such that the system includes the patient identification device and the plurality of the medical devices all attach externally to the patient, the patient identification device communicating with the plurality of medical devices concurrently.

18. The system as set forth in claim 16, further including a plurality of the patient identification devices corresponding to each of a plurality of patients and at least one of the medical devices corresponding to each of the plurality of patients, such that each of the plurality of patients is attached to one of the patient identification devices and at least one of the medical devices.

19. The system as set forth in claim 16, wherein the medical device processor further controls the medical device transmitter to transmit an alarm signal to the monitor in response to the received patient identification code failing to match the stored patient identification code.

* * * * *